United States Patent
Taheri et al.

(10) Patent No.: US 6,690,970 B1
(45) Date of Patent: Feb. 10, 2004

(54) BIOLOGICAL PACEMAKER AND IMPLANTATION CATHETER

(76) Inventors: Syde A. Taheri, 1275 Delaware Ave., Buffalo, NY (US) 14209; Howard J. Leonhardt, 2400 N. Commerce Pkwy., Suite 498, Weston, FL (US) 33326

(*) Notice: Subject to any disclaimer, the term of this patent is extended or adjusted under 35 U.S.C. 154(b) by 352 days.

(21) Appl. No.: 09/684,464

(22) Filed: Oct. 6, 2000

(51) Int. Cl.[7] .......................... A61N 1/18; A61K 35/44
(52) U.S. Cl. .......................................... 607/9; 424/569
(58) Field of Search .................. 607/2, 3, 4, 5, 607/9, 10, 115, 119, 123; 424/569

(56) References Cited

U.S. PATENT DOCUMENTS

| | | | |
|---|---|---|---|
| 4,245,624 A | 1/1981 | Komiya | 128/4 |
| 5,103,821 A | 4/1992 | King | 128/419 |
| 5,324,519 A | 6/1994 | Dunn et al. | 424/426 |
| 5,425,705 A | 6/1995 | Evard et al. | 604/28 |
| 5,456,694 A | 10/1995 | Marin et al. | 606/198 |
| 5,507,802 A | 4/1996 | Imran | 607/128 |
| 5,571,083 A | 11/1996 | Lemelson | 604/51 |
| 5,634,895 A | 6/1997 | Igo et al. | 604/21 |
| 5,941,845 A | 8/1999 | Tu et al. | 604/53 |
| 6,059,726 A | 5/2000 | Lee et al. | 600/439 |
| 6,151,525 A * | 11/2000 | Soykan et al. | 607/50 |
| 6,238,429 B1 * | 5/2001 | Markowitz et al. | 607/116 |
| 6,271,211 B1 * | 8/2001 | Christ et al. | 514/44 |
| 6,348,050 B1 * | 2/2002 | Hartlaub | 604/891.1 |
| 6,406,693 B1 * | 6/2002 | Thorpe et al. | 424/130.1 |

* cited by examiner

*Primary Examiner*—Sang Y. Paik
(74) *Attorney, Agent, or Firm*—Walter W. Duft (57) ABSTRACT

A biological pacemaker and implantation catheter for restoring normal or near normal heartbeat function without a mechanical pacemaker. The biological pacemaker is provided by a bridge of implantation cells, such as nerve cells, stem cells or ganglion cells, that are introduced into an area of electrical malfunction, such as an impaired SA node or a blocked AV node. The implantation cells grow to form a conductive cell bridge around the malfunction area so that a new pathway is provided for the electrical signals responsible for triggering heart beat contractions. The implantation catheter has a central nerve cell injection needle connected to a syringe or the like via a cell injection tube, and two elongated lateral stabilizing needles. The catheter is inserted into a blood vessel in a patient's leg, arm, shoulder or the like, and advanced until the catheter's distal end is located above the malfunction area. The distal end of the catheter is bent so that the three needles are facing the malfunction area. The two stabilizing needles are advanced into the heart wall to stabilize the catheter and the nerve cell injection needle is advanced for injection of the implantation cells.

3 Claims, 12 Drawing Sheets

BIOLOGICAL PACEMAKER AND IMPLANTATION CATHETER

CROSS-REFERENCE TO RELATED APPLICATIONS

Not Applicable

STATEMENT REGARDING FEDERALLY SPONSORED

RESEARCH OR DEVELOPMENT

Not Applicable

BACKGROUND OF THE INVENTION

1. Field of the Invention

This invention relates to cardio myopathy and its effect on electrical activity of the heart. More particularly, the invention concerns a pacemaker and related instrumentation for restoring heart rhythtn functionality to a heart.

2. Description of the Prior Art

By way of background, the human heart is a large muscle consisting of a series of pumping chambers that are carefully controlled by a specialized electrical system designed to deliver timed contraction signals to the muscle cells associated with each chamber. This electrical system attempts to regulate the heart rate between a range of about 60–100 beats per minute. At the beginning of a heart beat, an electrical signal originates near the top of the right atrium. A network of specialized nerve cells, known as the "sino-atrial" or SA node, generates the electrical signal. Conduction pathways carry the electrical signal to the muscle cells of the left and right atria, causing them to contract and pump blood into the ventricles. Additional conduction pathways carry the electrical signal in a downward fashion to additional nerve tissue known as the "atrio-ventricular" or AV node. Here the electrical signal is slowed slightly as the ventricles fill with blood. The AV node electrically separates the upper and lower chambers of the heart and acts as a gateway to an additional bundle of conductor cells known as the "bundle of His." The bundle of His divides into right and left branches in the lower chambers of the heart to carry the electrical signal to two final groups of nerve tissue, known as the Purkinje fibers. The Purkinje fibers on the left and rights side of the heart respectively deliver the electrical signal to the muscle cells of the left and right ventricles. Because of the specialized way in which the electrical signal is transmitted, the ventricles contract almost simultaneously.

With normal electrical conduction, the cardiac contractions are very organized and timed so that the atria contract before the ventricles, and the heart rate is maintained between about 60 and 100 beats per minute. This provides the major pumping action of the heart, allowing blood supply to reach the tissues of the body.

Sick sinus syndrome is a condition in which the SA node is impaired, such that a heart rhythm disturbance results. In particular, the SA node loses the ability to initiate a heartbeat or increase the heart rate, and the heart may not be able to respond effectively to the body's changing circulation demands. Heart block is a condition in which the tissue constituting the AV node is impaired and the electrical impulse from the upper portion to the lower portion of the heart is slowed, blocked or made irregular, such that ventricular contraction is slowed. A common cause of sick sinus syndrome and heart block is nerve cell damage caused by a heart attack or other cardio myopathic condition. Other causes may also produce these conditions. The treatment is usually the implantation of a mechanical pacemaker in the patient's upper right shoulder, with one or more shielded leads being attached to the heart to generate electrical signals that pace the heart at a suitable rate.

Although many advances have been made in the implantable pacemaker art, a number of disadvantages still exist. Pacemaker implantation, for example, is generally expensive and typically requires hospitalization, operating-room time, and post-operative observation. The treatment is also associated with some risk. A pacemaker, moreover, although capable of increasing its electrical output under changing conditions, such as exercise, cannot alter its signal generation rate as efficiently as the heart's own electrical system. It is also necessary to replace a pacemaker every 5–7 years insofar as such devices run on batteries.

It would be desirable if the foregoing disadvantages of existing implantable pacemakers could be overcome. What would be particularly useful is a pacemaker that is (1) readily implantable, preferably without surgery, (2) operates virtually indefinitely without replacement, and (3) provides normal or near normal heart rhythm functionality, including the ability to produce rapid changes in heart rate when necessary.

U.S. Pat. No. 5,103,821 (the '821) discloses a method of providing biological pacemaker as an alternative to mechanical pacemakers. In accordance with the disclosed method, SA node cells are removed from the heart and cultured to generate a critical mass of SA node cells of sufficient quantity to generate a depolarization wave capable of stimulating the cells of the myocardium to ensure normal or near normal pumping action in the heart. The critical mass of SA node cells are then implanted in the myocardial tissue of the right ventricle, preferably near the ventricular apex, to provide biological pacing for the heart which is sensitive to and variable with normal increase and decrease of output demands on the heart. A new SA node is essentially created and it is said that the heart's natural SA node may need to be destroyed in some cases to prevent "cross-talk" between the newly implanted SA node cells and those remaining in the right atrium.

A deficiency of the method disclosed in the '821 patent is that it involves the recreation of an SA node at a new location in the heart. This may affect the heart's pumping action insofar as SA node activity is now occurring in the right ventricle rather than the right atrium. Moreover, the above-mentioned cross-talk may occur unless the original SA node is completely removed. A further deficiency of the method of the '821 patent is that it requires the use of three different catheters to perform the procedure. A locating catheter is required to locate the existing SA node so that SA node cells can be removed for culturing. A removal catheter is used to remove the SA node cells. An implant catheter is used to implant the cultured SA node cells in the right ventricle.

Applicants submit that improvements in biological pacemaker technology are needed. In particular, it would be desirable if dysfunctional SA node tissue (or AV node tissue) could be treated in situ and restored to normal or near normal activity rather recreating node functionality at an entirely new location, and possibly destroying the original node. A multi-purpose catheter that can be used for both node mapping and cell implantation, or for node mapping and cell removal, or perhaps for all three functions of mapping, removal and implantation, would also be desirable.

SUMMARY OF THE INVENTION

The foregoing problems are solved and an advance in the art is obtained by a biological pacemaker and implantation catheter for restoring normal or near normal heartbeat function without a mechanical pacemaker. The biological pacemaker is provided by a bridge of implantation cells, such as cultured autologous SA or AV node cells, nerve cells, stem cells, or ganglion cells, that are introduced into an area of electrical malfunction, such as an impaired SA node or a blocked AV node. The implantation cells grow to form a conductive cell bridge around the malfunction area so that a new pathway is provided for the electrical signals responsible for triggering ventricular contractions. The impaired node is thus repaired and not rebuilt at a new location as in the '821 patent described by way of background above.

The implantation cells can be introduced into the malfunction area in any suitable fashion, but are preferably injected via an improved catheter that can be used for both node mapping and cell implantation. The catheter has a central nerve cell injection needle connected to a syringe via a cell injection tube, and two elongated lateral stabilizing needles. The catheter further includes instrumentation for locating a blocked SA or AV node by way of electrical, ultrasound and/or visual probing. Further instrumentation can be added for cell removal.

The catheter is inserted into a blood vessel in a patient's leg, arm, shoulder or the like, and advanced until the catheter's distal end is located adjacent to the malfunction area. The catheter is constructed so that its distal end can be bent so that the three needles are facing the malfunction area, which is located using the catheter's locating equipment. The two stabilizing needles are advanced into the heart wall to stabilize the catheter and the nerve cell injection needle is advanced to inject the implantation cells. The nerve cells are injected via the syringe.

The catheter can be bent using a pull cable that is attached to the catheter's distal end, and which may run inside a cable sheath back to the catheter's proximal end. The two lateral stabilizing needles are flexible needles that may be connected together as a unit by way of one or more needle guides. The guides preferably have a central aperture for receiving the cell injection tube that runs from the syringe to the cell injection needle. An injection tube sheath can be mounted to extend between the apertures for slidably receiving the cell injection tube. The catheter can be made from plastic tube material but most preferably has two walls defining a main hydraulic sheath that can be filled with saline or water. The main hydraulic sheath is filled to stiffen the catheter during insertion. At least the distal end thereof can then be emptied to allow the distal end to be bent. During insertion of the catheter into a patient, all of the needles are retracted. When the distal end of the catheter has been positioned adjacent the block site, the tip of the catheter is bent and the lateral stabilizing needles are extended to pierce the heart wall. To facilitate bending, the pressure in the main hydraulic sheath can be relieved. The stabilizing needles stabilize the catheter against the movement of the beating heart. The cell injection tube and needle are then extended to inject the nerve cells. Preferably, a small bladder at the distal end of the hydraulic sheath remains pressurized with fluid to form a seal against leakage during nerve cell implantation.

BRIEF DESCRIPTION OF THE DRAWING

The foregoing and other features and advantages of the invention will be apparent from the following more particular description of preferred embodiments of the invention, as illustrated in the accompanying Drawing, in which.

DETAILED DESCRIPTION OF THE PREFERRED EMBODIMENT

Figure 1:
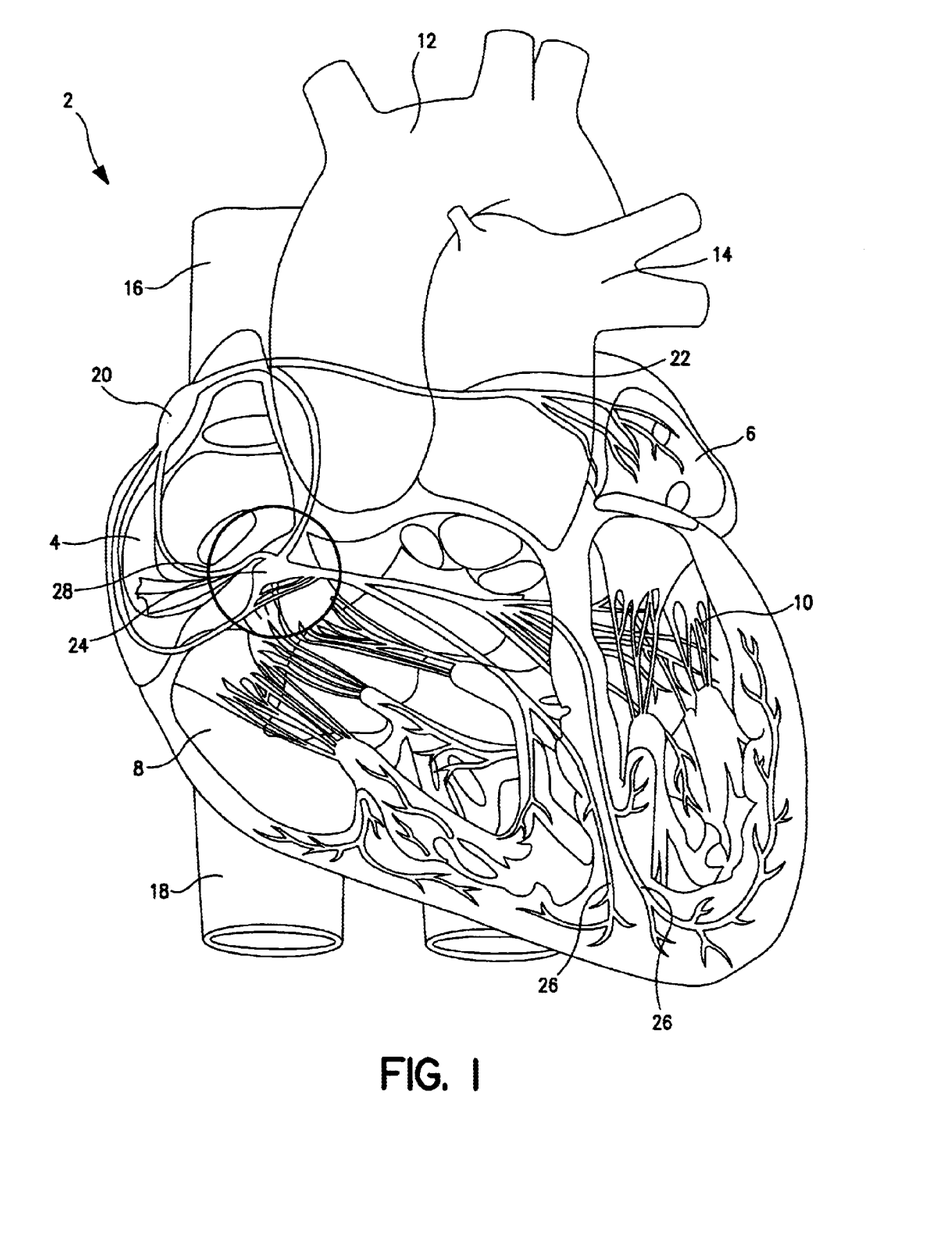
FIG. 1 is a sectioned diagrammatic view of a heart showing a blocked AV node.

Turning now to the figures, wherein like reference numerals represent like elements in all of the several views, FIG. 1 illustrates a human heart 2 that has been sectioned to show the four pumping chambers. In particular, the heart 2 has a right atrium 4, a left atrium 6, a right ventricle 8 and a left ventricle 10. Also shown are an aorta 12, a pulmonary artery 14, a superior vena cava 16 and an inferior vena cava 18. The heart 2 is also shown as having an electrical system that includes an SA node 20 and an upper conductive pathway system 22. The heart's electrical system further includes an AV node 24 and a lower conductive pathway system 26 (comprising the bundle of His and the Purkinje fibers) for carrying electrical signals from the AV node 24 to the muscles of the ventricles. FIG. 1 further shows a circular region 28 that is assumed to encompass an area of AV node blockage (block site) that is disrupting the SA node's electrical signals on their way to the lower conductive pathways 26, creating the condition known as heart block. This blockage area is shown in detail by reference numeral 30 in FIG. 2.

Figure 2:
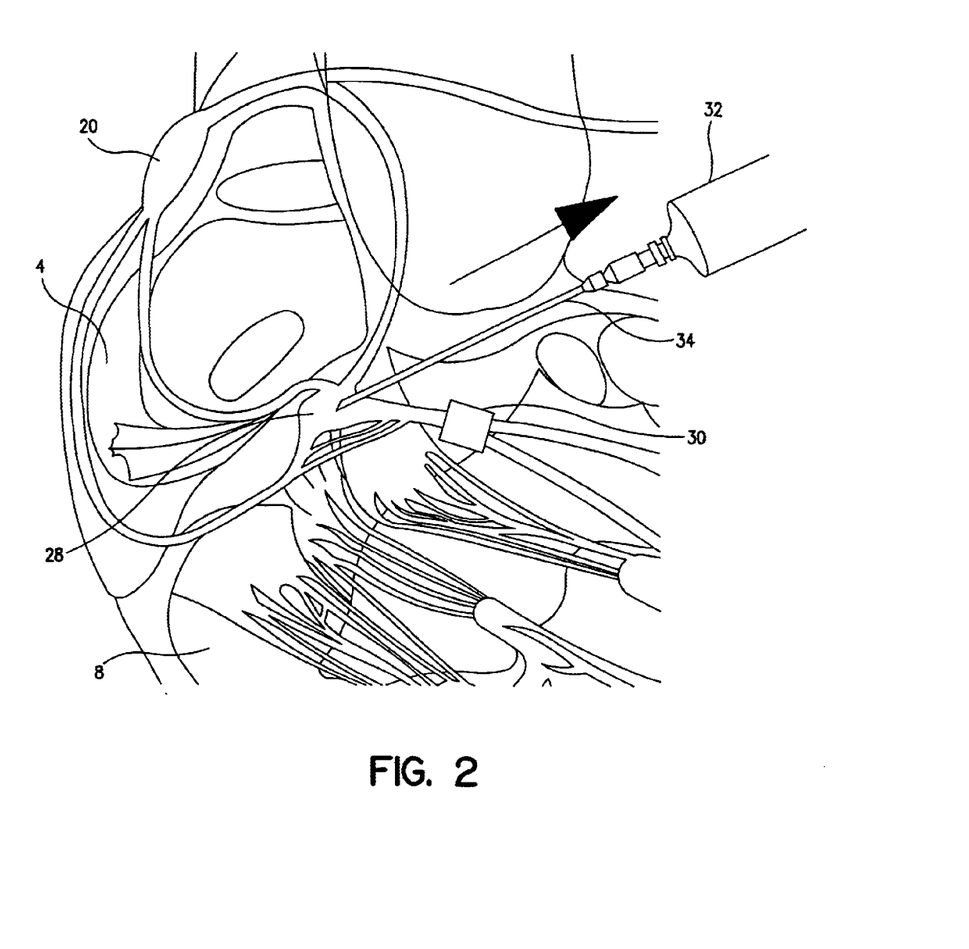
FIG. 2 is a sectioned diagrammatic view showing the aspiration of autologous conductive cells during mapping of the blocked AV node.
Figure 3:
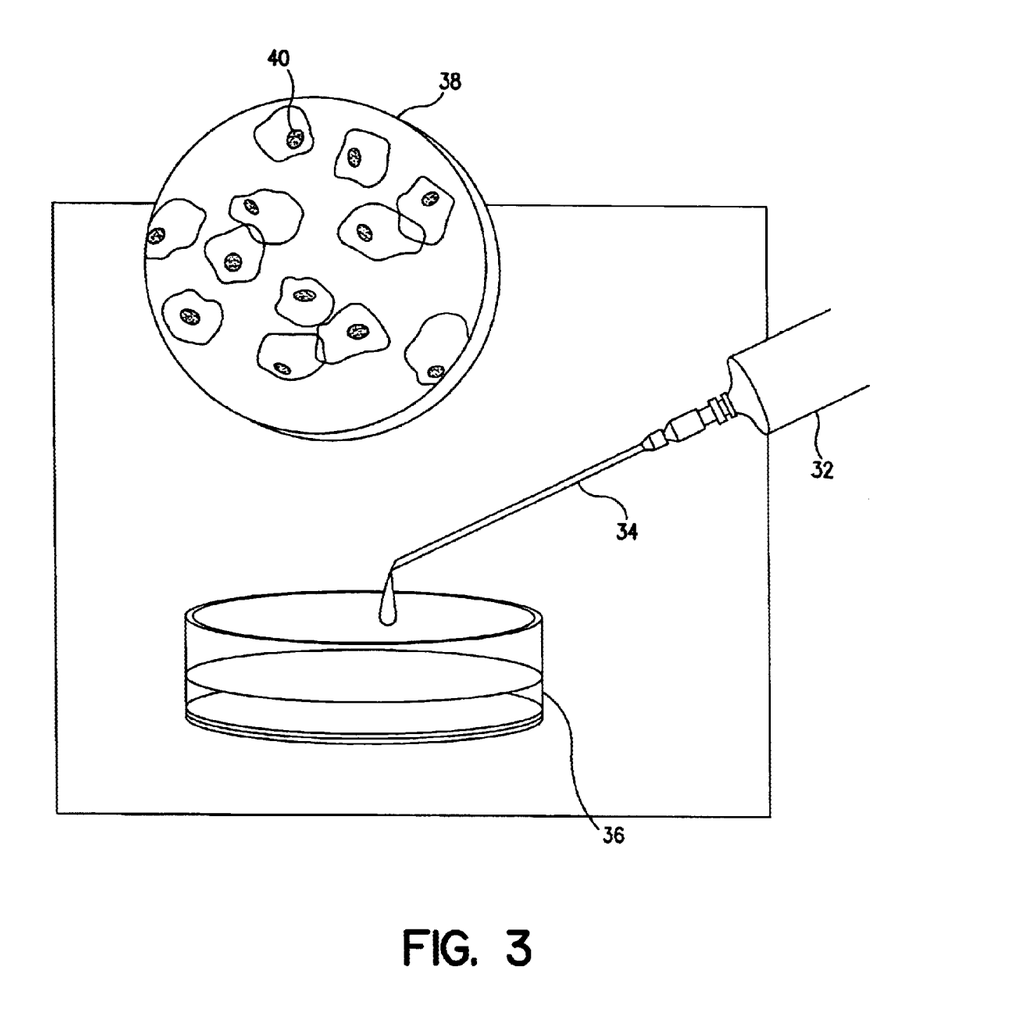
FIG. 3 is a diagrammatic view showing a culture of autologous conductive cells.
Figure 4:
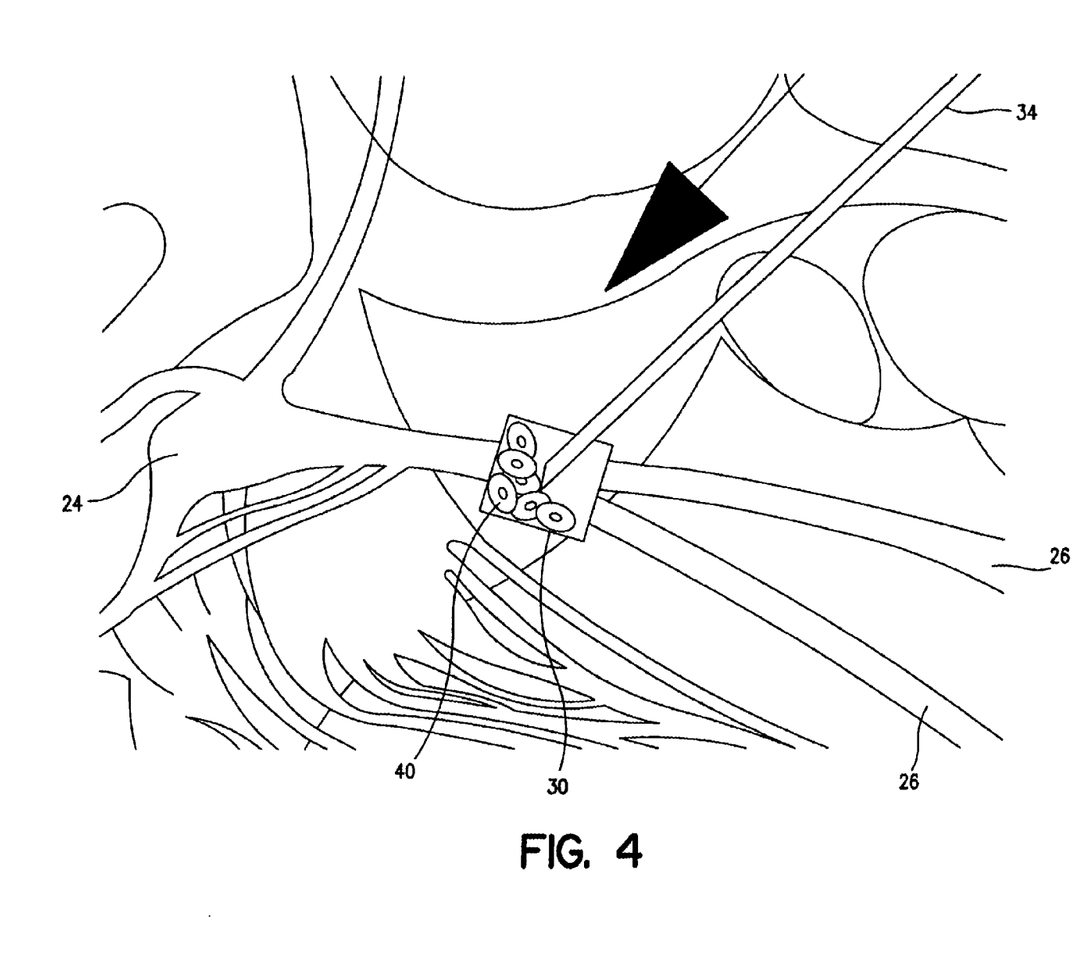
FIG. 4 is a diagrammatic view of showing the introduction of conductive cells into an area of blockage in an AV node.

In accordance with the biological implantation procedure of the invention, implantation cells are obtained a suitable source. Such sources may include nerve cells obtained from peripheral sensory nerves, ganglion cells obtained from the lumbar or cervical region, and stem cells obtained from bone marrow, skin, umbilical vein or embryo tissue. It is further noted that the introduction of about 200 picoamps (for normal cells) and 700 picoamps (for transformed cells) of electricity to SA or AV node cells can cause them to dedifferentiate to their original embryonic form. Cells that have been genetically altered to produce atropine or otherwise accelerate heart rate in response to increases in patient activity could also be used. Most preferably, however, the implantation cells are either conduction cells obtained from a well-matched homologous AV node (or SA node) donor or autologous cardiac conduction cells that have been cultured. The autologous cardiac conduction cells may be obtained from the patient by aspiration of the conductive system during mapping of the AV node, as shown in FIG. 2. Aspiration may be performed using a syringe 32 having an aspiration needle 34, or an intravenous biopsy catheter of conventional design. FIG. 3 shows the aspirated AV node cells being placed in a cell dish 36 so that a cell culture 38 containing a suitable quantity of implantation cells 40 (e.g., about $10^8$–$10^9$ cells) is generated.

Additional implantation cell options include mixing or transvecting a gene that expresses connexin 43 protein with existing SA or AV node cells. This can serve to promote the formation of gap junctions, which are essential for electrical connection to existing myocardial cells. Existing SA or AV node cells can also be mixed with myoblasts that will ultimately form muscle fibers to help connect the conduction cells to the myocardium. According to another alternative, SA or AV node cells can be mixed or transvected with VEGF (Vascular Endothelial Growth Factor) or FGF (Fibroblast Growth Factor) to stimulate angiogenesis to feed blood to the newly implanted cells. According to still another alternative, SA or AV node cells can be mixed or transvected with eNOS (endothelial Nitric Oxide Synthase) for producing large diameter, longer and more functional (endothelium-lining) blood vessels (arteriogenesis) for feeding the newly injected conduction cells. In a still further alternative, SA or AV node cells can be mixed or transvected with Ang 1 (Angiopoiten 1 Tie receptors), which will also aid the neovascularization process.

With respect to the culturing of implantation cells, it is submitted that higher quality cells can be obtained by mixing them with embryonic or mesenchymal stem cells or immature myoblasts in the cultured medium. Electrical connections can be promoted by stimulating the cells with electricity or introducing the aforementioned connexin 43 protein. It is further submitted that the implantation cells can be conditioned to maintain a certain beat rate by introducing pacing leads from an electrical pacemaker into the culture dish holding the cultured medium.

Figure 5:
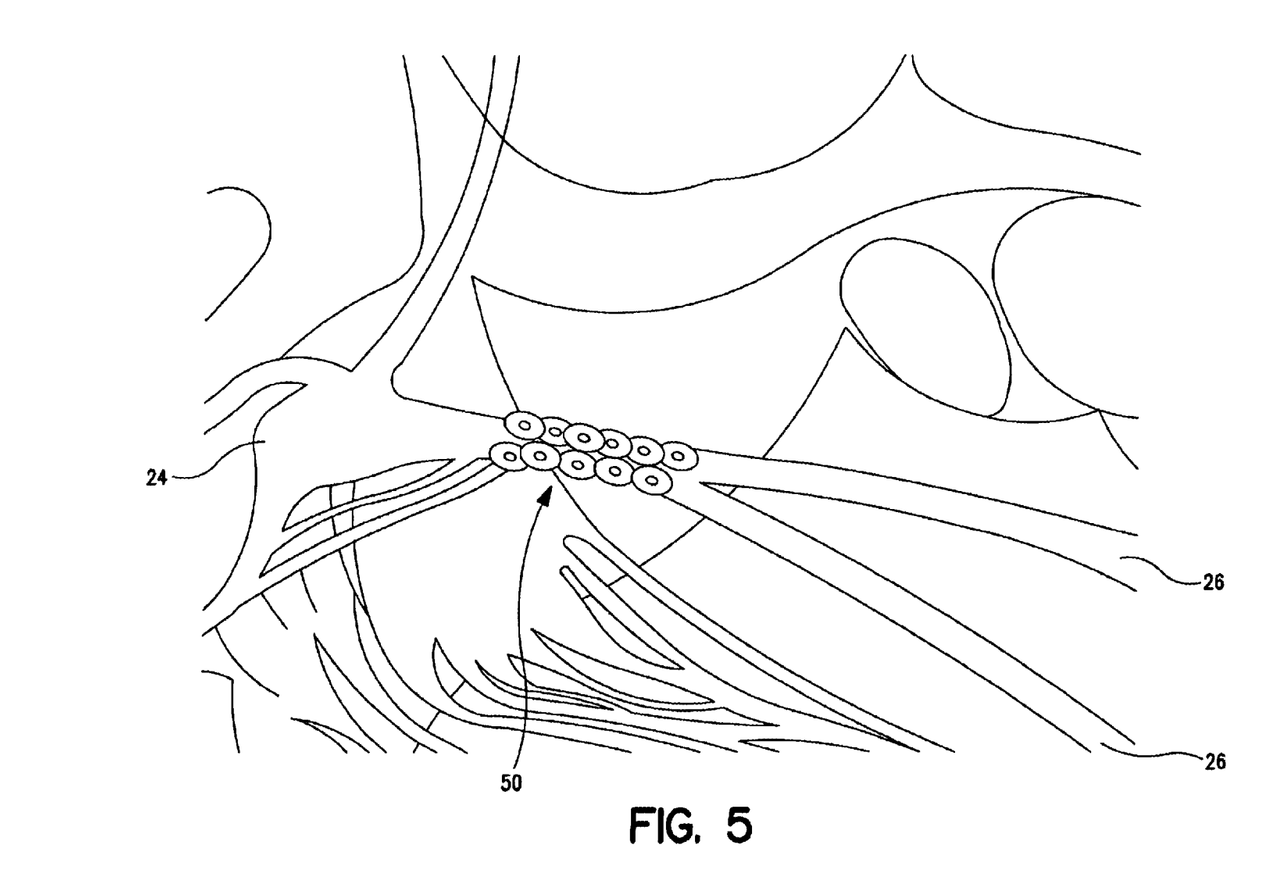
FIG. 5 is a diagrammatic view showing a newly formed conductive cell bridge across an area of blockage in an AV node.
Figure 6:
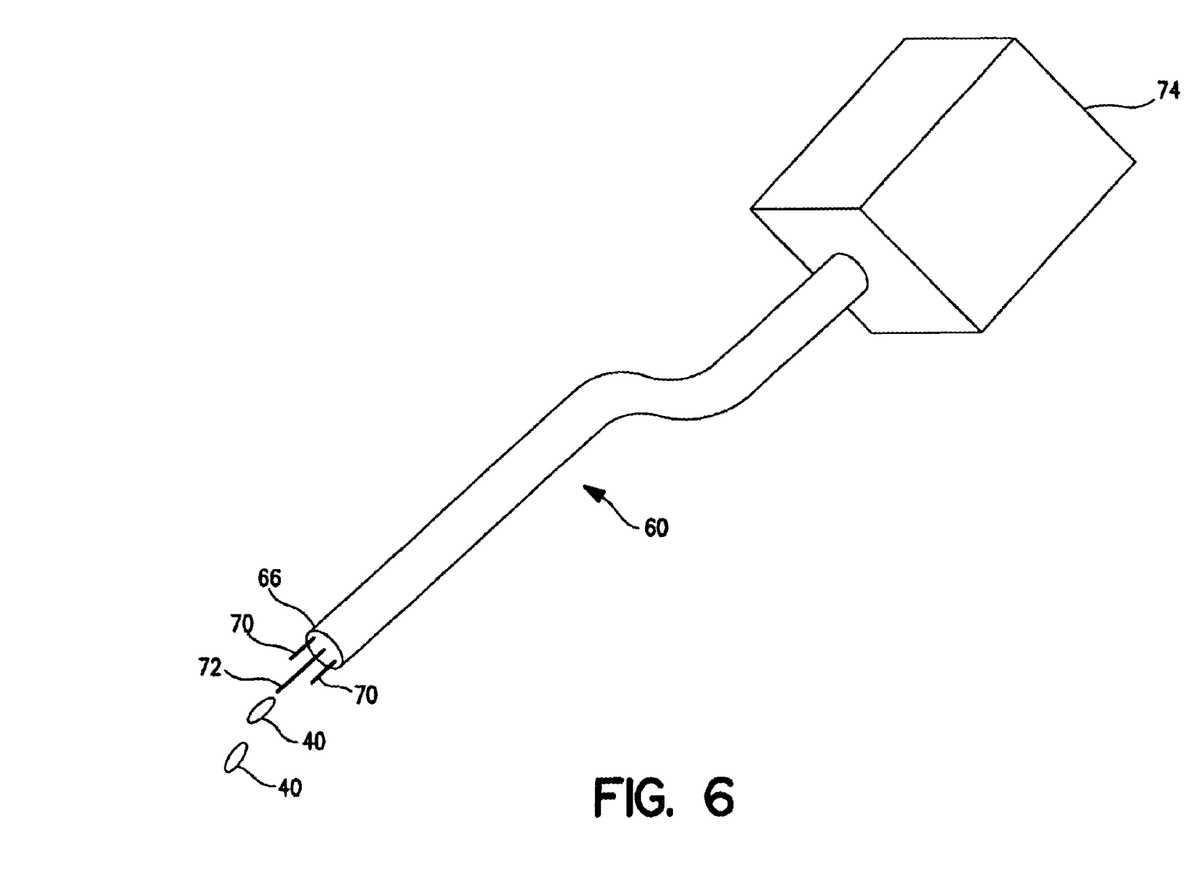
FIG. 6 is a perspective view of a catheter for injecting conductive cells into an area of AV node blockage.

After determination of the location of the block site 30 in FIG. 2, a plurality of the implantation cells 40 are implanted (seeded). Implantation may be performed by injection using the needle 34, but is preferably performed using the catheter described in more detail below. This same catheter is also preferably used for block site mapping, and may likewise be adapted for cell removal. As shown in FIG. 5, the implantation cells 26 grow to form a conductive cell bridge 50. One end of the cell bridge 50 connects to healthy tissue on one side of the block site 30 while the other end of the cell bridge connects to healthy tissue on the other side of the block site 30. The cell bridge 50 allows electric potential to pass through the block site 30 and reach the ventricular muscles.

For patients that have suffered a myocardial infarction (MI), an additional procedure would be to mix immature myoblasts with one or more of eNOS, Ang 1, VEGF, FGF, pyruvate, and L-Arginine amino acid, together with SA or AV node cells, and inject the mixture to create a bridge that connects from the center of the MI scar to the existing AV node, or alternatively to the existing SA node. This will assure that the repaired scar area beats in synchrony with the rest of the heart.

An implantation catheter 60 for mapping the block site 30 and injecting the implantation cells 26 therein can be constructed as shown diagrammatically in FIGS. 6–12. The catheter 60 has an exterior sheath 62 having aproximal end 64 and a distal end 66. Extending through the exterior sheath 62 is a central nerve cell injection tube 68 (see FIGS. 10A, 10B and 10C) and two elongated lateral stabilizing needles 70. The distal end of the injection tube 68 connects to an implantation cell injection needle 72, while the proximal end mounts to a control unit 74 that includes a syringe or the like for injecting a solution containing implantation cells through the injection tube 68 to the injection needle 72. The distal ends of the stabilizing needles 70 are pointed. Their proximal ends are suitably configured for manual manipulation by a surgeon operating the control unit 74. The stabilizing needles 70 stabilize the catheter's distal end 66 during cell implantation. In addition, as described in more detail below, they can also be used as electrical probes for electromapping the block site 30.

Figures 7A, 7B:
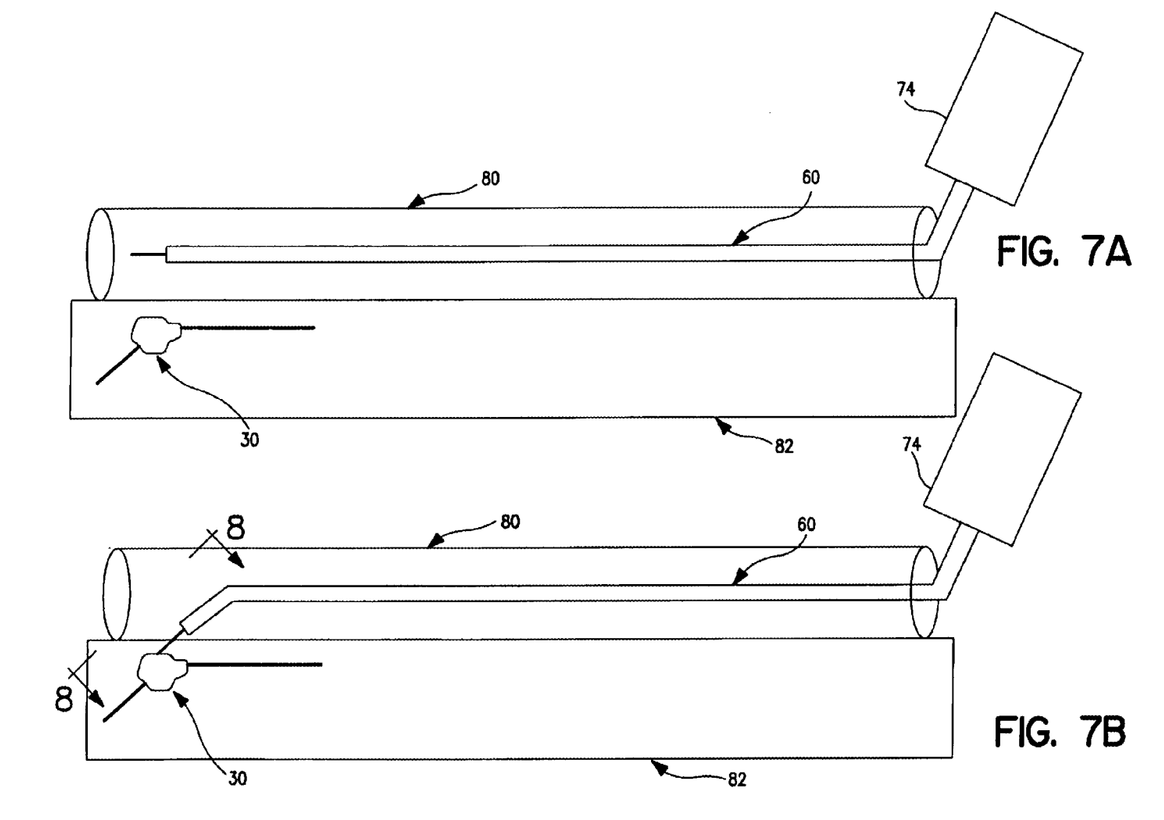
FIG. 7A is a diagrammatic side view of the catheter of FIG. 6 with its distal end located above an area of blockage in an AV node.
FIG. 7B is a diagrammatic side view of the catheter of FIG. 6 with its distal end positioned for the injection of conductive cells into an area of blockage in an AV node.
Figure 8:
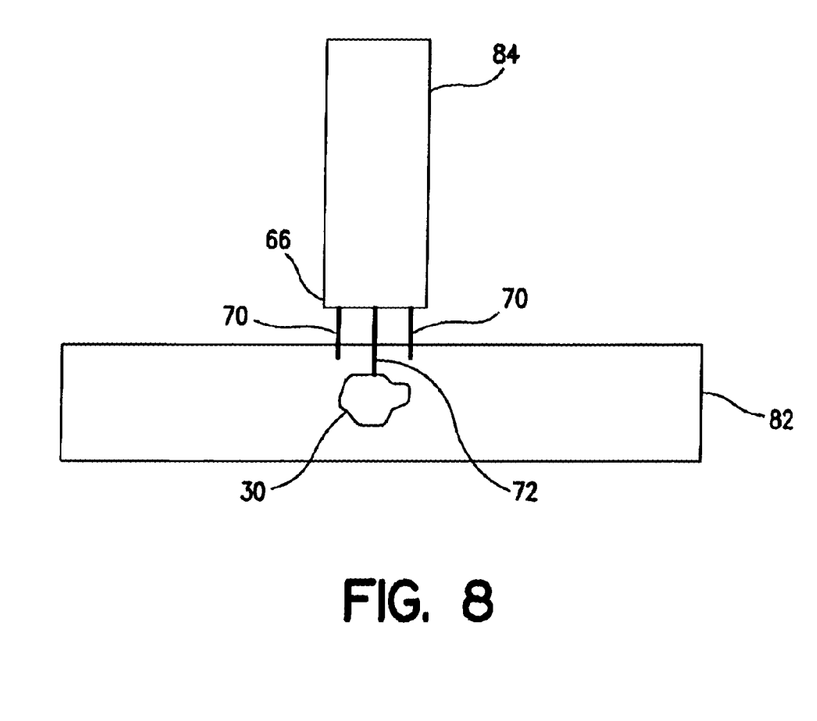
FIG. 8 is a diagrammatic view taken in the direction of arrows 8—8 in FIG. 7B showing the injection of conductive cells into an area of blockage in an AV node.
Figure 9A:
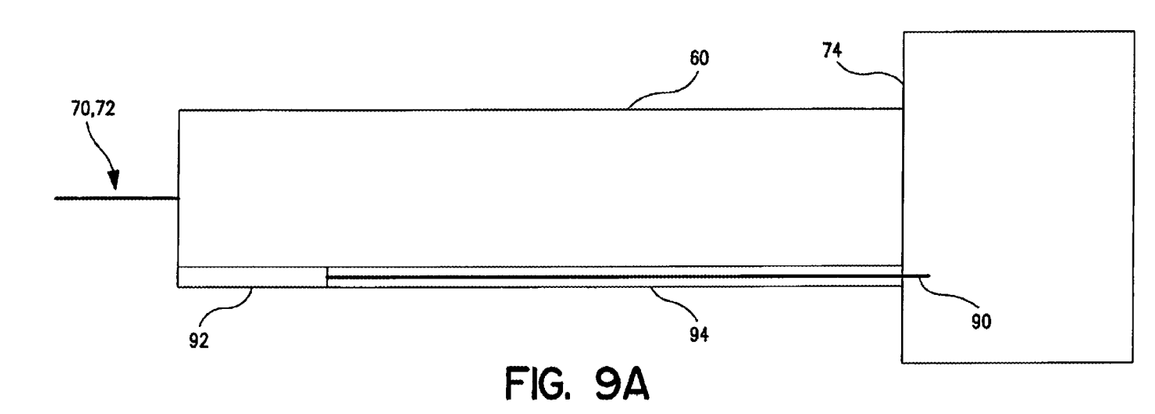
FIG. 9A is a diagrammatic side view of the catheter of FIG. 6 prior to bending of the distal end thereof.
Figure 9B:
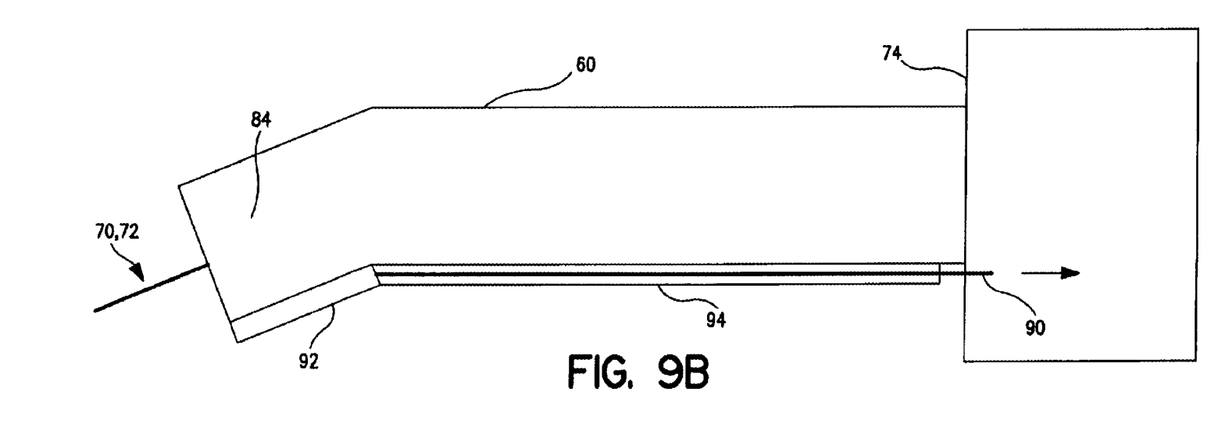
FIG. 9B is a diagrammatic side view of the catheter of FIG. 6 following bending of the distal end thereof.

Turning now to FIGS. 7A and 7B, the catheter 60 is inserted into a blood vessel in a patient's leg, arm, shoulder or the like, and advanced until the catheter's distal end extends through a suitable coronary artery 80 until the distal end 66 is located adjacent to the portion of the myocardium 82 that contains the block site 30. Mapping instrumentation mounted on the catheter 60 (described in more detail below) is used to locate the block site. Once the catheter's distal end 66 is positioned at the proper location, the catheter 60 is bent at a distal bending section 84 thereof so that the stabilizing needle pair 70 and the injection needle 72 are facing the block site. The stabilizing needles 70 are then advanced into the myocardium to stabilize the catheter 60 and the injection needle 72 is advanced into the block site 30, as shown in FIG. 8. As shown in FIGS. 9A and 9B, the catheter 60 can be bent using a pull cable 90 that is suitably attached at 92 to the catheter's bending section 84, and which may run inside a sheath 94 back to the control unit 74 at the catheter's proximal end 64.

Turning now to FIGS. 10A, 10B, 10C and 11, the catheter 60 is illustrated in more detail although it will be appreciated that many of the conventional components thereof, and particularly those found on the control unit 74, have not been shown for clarity. It will also be understood that FIGS. 10A, 10B, 10C and 11 are intended to be diagrammatic in nature and not necessarily illustrative of any particular component shape or configuration. With the foregoing in mind, it will be seen that the stabilizing needles 70 are elongated flexible needles that are connected together as a unit by way of one or more needle guides 100 (two are shown) or the like. The guides 100 may have a central aperture 102 for receiving the cell injection tube 68 that runs from the syringe 74 to the cell injection needle 72. An injection tube sheath 104 can also be mounted to extend between the apertures 102 for slidably receiving the cell injection tube 68. The catheter 60 can be made from plastic tube material but most preferably has inner and outer walls 110 and 112, respectively, defining a main hydraulic sheath 114 that can be filled with a suitable hydraulic fluid 115, such as saline or water. The main hydraulic 114 sheath can be filled with the hydraulic fluid 1 15 via an inlet 116 to stiffen the catheter 60 during insertion thereof through a blood vessel. The main hydraulic sheath 114 can then be at least partially emptied until the portion of the main hydraulic sheath 114 that forms the catheter's bending section 84 can be bent in the manner described above.

Figure 10A:
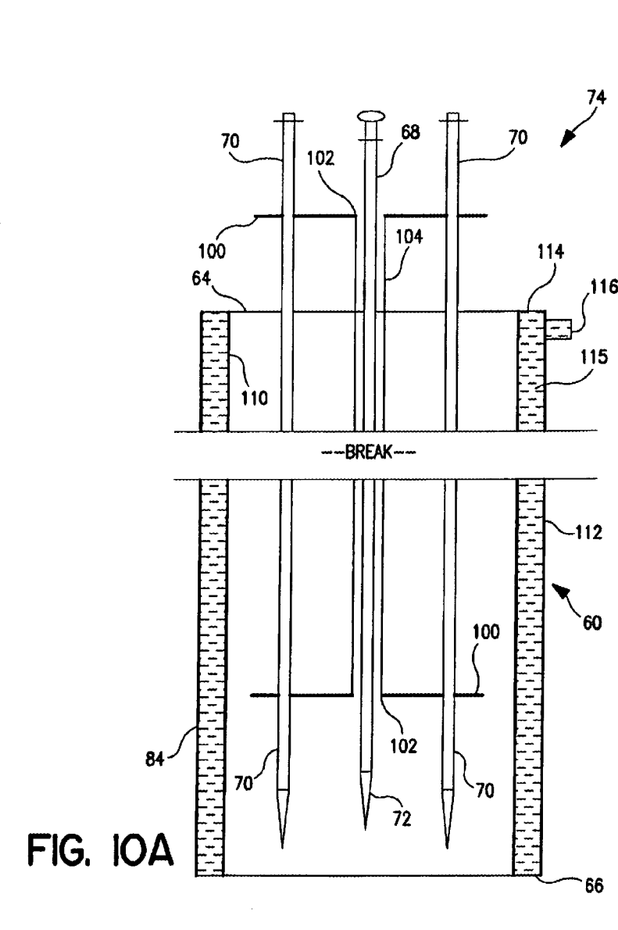
FIG. 10A is a partial diagrammatic sectional view of the catheter of FIG. 6 in a first orientation used for insertion of the distal end thereof toward an area of AV node blockage.
Figure 10B:
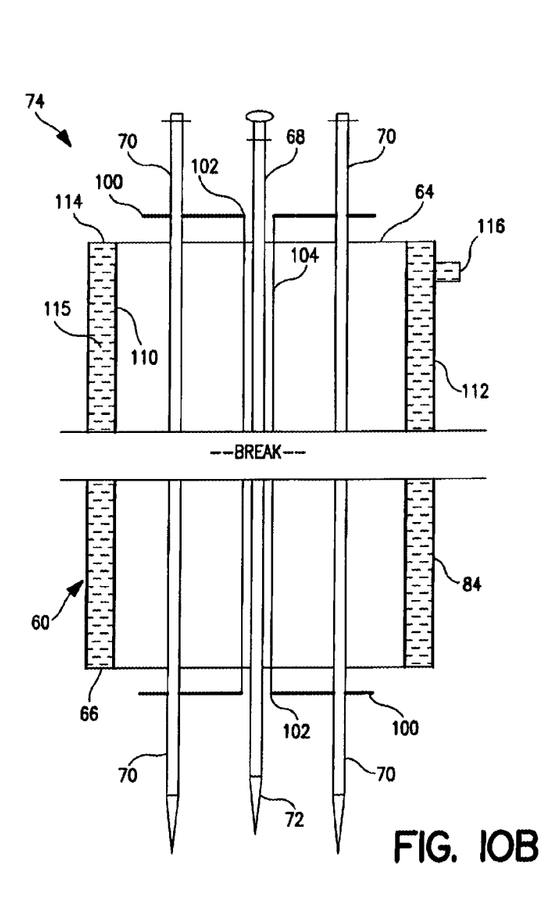
FIG. 10B is a partial diagrammatic sectional view of the catheter of FIG. 6 in a second orientation used to stabilize the distal end thereof prior to the injection of conductive cells into an area of AV node blockage.
Figure 10C:
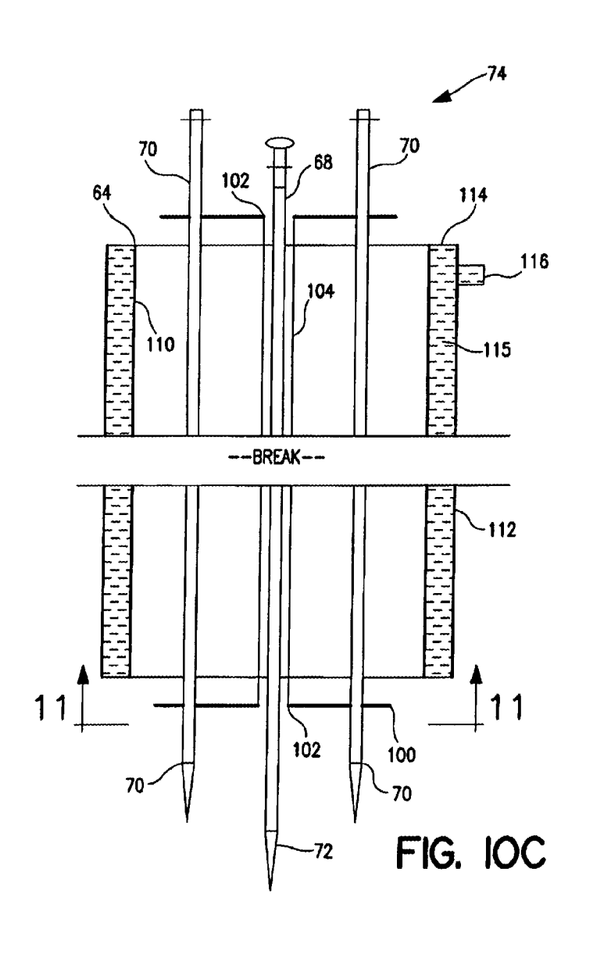
FIG. 10C is a partial diagrammatic sectional view of the catheter of FIG. 6 in a third orientation used to inject conductive cells into an area of AV node blockage.
Figure 11:
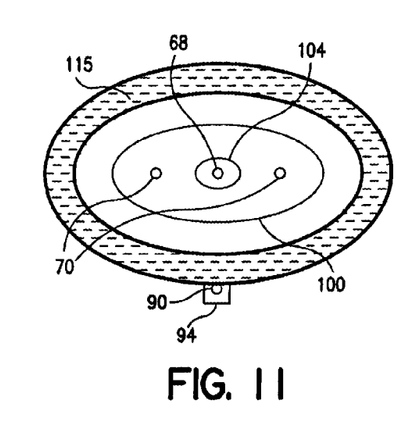
FIG. 11 is a cross-sectional view taken along line 11—11 in FIG. 10C.

FIGS. 10A, 10B and 10C further show the positioning of the stabilizing needle pair 70 and the injection needle 72 during implantation. In FIG. 10A, all of the needles are retracted so that the catheter 60 can be inserted into the patient. In FIG. 10B, the two lateral stabilizing needles 70 are extended to pierce the myocardium. In FIG. 10C, the cell injection tube 68 and the cell injection needle 72 are extended to inject the implantation cells 30. The foregoing positioning sequence is accomplished using the control unit 74, which will understood to include suitable controls connected to the needles and guide elements shown in the figures. In particular, one or more first controls will be provided to advance and retract the lateral stabilizing needles 70 and their associated needle guides 100, and one or more second controls will be provided to advance and retract the injection needle 72 relative to the lateral stabilizing needles, and to inject implantation cells. Additional controls will be provided to control the hydraulic sheath 114 and to bend the catheter's distal end 66.

As previously stated, the lateral stabilizing needles 70 can be connected to electro-mapping equipment (not shown) at their proximal ends and used to map the location of the block site 30. During this procedure, the lateral stabilizing needles 70 will be at least partially extended into the myocardium so that electrical current is discharged therein. The connected electro-mapping equipment will then measure changes in the current to determine the existence of areas of node damage. Note that the lateral stabilizing needles 70 can act as ECG (ElectroCardioGram) electrodes as well as MAP (Monophsic Action Potential) probes. In the ECG mode, the electro-mapping equipment connected to the lateral stabilizing needles 70 can communicate with a personal computer or the like running a software package such as the LocaLisa® program from Medtronic, Inc. This software allows the medical practitioner to obtain a full colorized electromagnetic map of the heart which can be used to pinpoint the exact location to inject implantation cells. In the MAP mode, the lateral stabilizing needles 70 can measure membrane potentials for NA, K, and CA, and help determine cell viability and the correct position to inject cells. As is known, MAP probes are less prone to regional noise than ECG electrodes and can sense deep into tissue, not just probe the surface. Once the block site 30 is mapped, the lateral stabilizing needles 70 can be more fully extended into the myocardium as necessary to achieve proper stabilization during the injection of the implantation cells.

Figure 12:
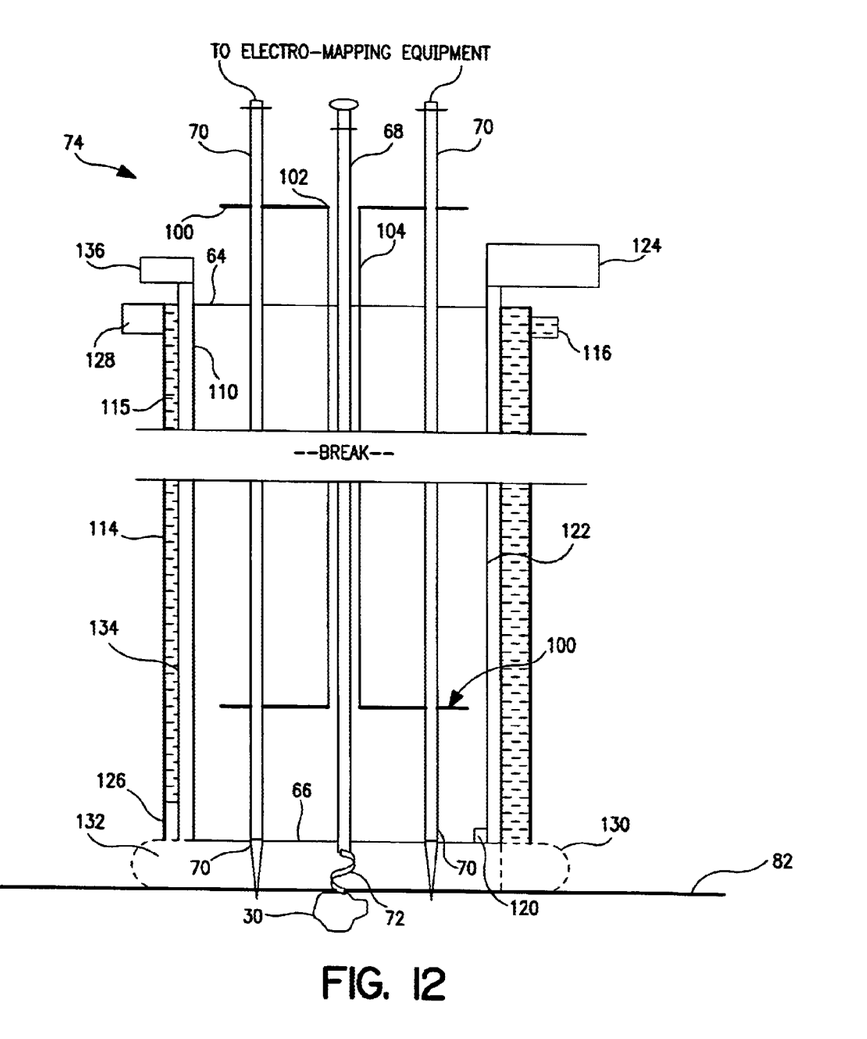
FIG. 12 is a partial diagrammatic sectional view of the catheter of FIG. 6 showing additional features thereof.

FIG. 12 shows that the catheter 60 may be equipped with additional instrumentation, such as an optical imaging device 120. The optical imaging device 120 can be mounted at the catheter's distal end 66 connected via a fiber optic bundle 122 to an optical viewing device 124 at the catheter's proximal end 64 for visually locating the block site 30. A Doppler wave probe 126 could also be mounted at the catheter's distal end 66 to detect myocardial blood vessel blockages, thus providing an additional mechanism for locating the block site 30. To that end, the hydraulic fluid 115 in the main hydraulic sheath 114 can be used as a propagation medium that carries the Doppler waves from a Doppler wave source 128 mounted at the catheter's proximal end 64 to the Doppler wave probe 124.

It will be further seen in FIG. 12 that the terminus of the main hydraulic sheath 114, representing the distal end 66 of the catheter 60, can be configured with a hydraulic bladder-type seal 130 that inflates to effectively extend the catheter and seal it against the myocardium 82. The seal 130 helps minimize implantation cell leakage during injection by surrounding the implantation needle 72 and enclosing the implantation area The seal 130 preferably uses a separate hydraulic chamber 132 that does not share hydraulic fluid with the main hydraulic sheath 114. In this way, the release of the hydraulic fluid 115 from the latter will not affect the seal's hydraulic pressurization. If desired, the seal 130 can be separately pressurized via a tube 134. This allows the seal 130 to be selectively depressurized during catheter insertion to minimize the seal's size, and then pressurized during cell injection. An inlet 136 can be located at the catheter's proximal end 64 for this purpose.

Another modification of the catheter 60 would be to add a cutting implement (not shown) so that catheter can be for the biopsy of autologous cardiac conduction cells. Catheter cutting instruments of this type are conventional. A still further modification of the catheter 60 (see FIG. 12) would be to configure the cell injection needle 72 with a corkscrew tip that can be slowly turned in and out of the myocardium (e.g., by rotating the injection tube 68) to provide a more stable introduction of implantation cells. This design also serves to trap more implantation cells (fewer cells lost through the entry hole) and serves to create the right type of injury to stimulate angiogenesis.

Accordingly, a biological pacemaker, an improved catheter and an associated pacemaker implantation method have been disclosed. While various embodiments of the invention have been described, it should be apparent that many variations and alternative embodiments could be implemented in accordance with the invention. It is understood, therefore, that the invention is not to be in any way limited except in accordance with the spirit of the appended claims and their equivalents.

What is claimed is:

1. A biological pacemaker for a heart having an area of electrical malfunction, comprising:

a bridge of implantation cells extending across said malfunction area;

said bridge having a first end implanted for connection to healthy conductive cells located at a first side of said malfunction area;

said bridge having a second end implanted for connection to healthy conductive cells located at a second side of said malfunction area;

said bridge having a continuous central portion implanted between said first and second ends;

said implantation cells being arranged to form a conductive pathway around said malfunction area for carrying electrical signals responsible for triggering contractions of said heart; and said implantation cells including SA or AV node cells that have been electrically stimulated to dedifferentiate them to embryonic form.

2. A biological pacemaker for a heart having an area of electrical malfunction, comprising:

a bridge of implantation cells extending across said malfunction area;

said bridge having a first end implanted for connection to healthy conductive cells located at a first side of said malfunction area;

said bridge having a second end implanted for connection to healthy conductive cells located at a second side of said malfunction area;

said bridge having a continuous central portion implanted between said first and second ends;

said implantation cells being arranged to form a conductive pathway around said malfunction area for carrying electrical signals responsible for triggering contractions of said heart; and said implantation cells including SA node cells or AV node cells mixed with embryonic cells.

3. A biological pacemaker for a heart having an area of electrical malfunction, comprising:

a bridge of implantation cells extending across said malfunction area;

said bridge having a first end implanted for connection to healthy conductive cells located at a first side of said malfunction area;

said bridge having a second end implanted for connection to healthy conductive cells located at a second side of said malfunction area;

said bridge having a continuous central portion implanted between said first and second ends;

said implantation cells being arranged to form a conductive pathway around said malfunction area for carrying electrical signals responsible for triggering contractions of said heart; and said implantations including SA node cells or AV node cells mixed with mesenchymal cells.

* * * * *